(12) United States Patent
Mustufa et al.

(10) Patent No.: US 11,819,301 B2
(45) Date of Patent: Nov. 21, 2023

(54) SYSTEMS AND METHODS FOR ONSCREEN MENUS IN A TELEOPERATIONAL MEDICAL SYSTEM

(71) Applicant: INTUITIVE SURGICAL OPERATIONS, INC., Sunnyvale, CA (US)

(72) Inventors: Tabish Mustufa, Sunnyvale, CA (US); Heath Feather, Cupertino, CA (US); Daniel H. Gomez, Los Gatos, CA (US); Brian D. Hoffman, Mountain View, CA (US); Paul W. Mohr, Mountain View, CA (US); Huan L. Phan, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/726,350

(22) Filed: Apr. 21, 2022

(65) Prior Publication Data
US 2022/0241039 A1   Aug. 4, 2022

Related U.S. Application Data

(60) Continuation of application No. 17/061,785, filed on Oct. 2, 2020, now Pat. No. 11,337,768, which is a
(Continued)

(51) Int. Cl.
*A61B 34/35* (2016.01)
*A61B 90/00* (2016.01)
(Continued)

(52) U.S. Cl.
CPC .............. *A61B 34/35* (2016.02); *A61B 34/25* (2016.02); *A61B 34/37* (2016.02); *A61B 34/74* (2016.02);
(Continued)

(58) Field of Classification Search
CPC ......... A61B 34/35; A61B 34/25; A61B 34/37; A61B 34/74; A61B 90/00; A61B 90/361
See application file for complete search history.

(56) References Cited

U.S. PATENT DOCUMENTS

| 6,468,212 B1 | 10/2002 | Scott et al. |
| 6,950,691 B2 | 9/2005 | Uchikubo |

(Continued)

FOREIGN PATENT DOCUMENTS

| EP | 1125557 A2 | 8/2001 |
| EP | 2939632 A1 | 11/2015 |

(Continued)

OTHER PUBLICATIONS

Extended European Search Report for Application No. EP17828100.2 dated 2 Feb. 8, 2020, 7 pages.
(Continued)

*Primary Examiner* — William D Titcomb
(74) *Attorney, Agent, or Firm* — HAYNES AND BOONE, LLP

(57) ABSTRACT

A teleoperational medical system comprises a teleoperational assembly including an operator control system, a first teleoperational manipulator, a first medical instrument, and a processing unit including one or more processors. The first teleoperational manipulators is configured for operation by an operator control device of the operator control system. The first teleoperational manipulator is configured to control the operation of the first medical instrument in a surgical environment. The processing unit is configured to display an image of a field of view of the surgical environment and display a menu proximate to an image of the first medical instrument in the image of the field of view. The menu includes at least one state indicator representing a state of a component of the first medical instrument.

22 Claims, 9 Drawing Sheets

Related U.S. Application Data division of application No. 16/316,981, filed as application No. PCT/US2017/029380 on Apr. 25, 2017, now Pat. No. 10,806,533.

(60) Provisional application No. 62/362,376, filed on Jul. 14, 2016.

(51) Int. Cl.
*A61B 34/00* (2016.01)
*A61B 34/37* (2016.01)
*A61B 17/00* (2006.01)

(52) U.S. Cl.
CPC ............ *A61B 90/00* (2016.02); *A61B 90/361* (2016.02); *A61B 2017/00199* (2013.01); *A61B 2017/00973* (2013.01); *A61B 2034/254* (2016.02); *A61B 2034/742* (2016.02)

(56) References Cited

U.S. PATENT DOCUMENTS

| 10,806,533 | B2* | 10/2020 | Mustufa | A61B 34/37 |
| 2006/0152516 | A1 | 7/2006 | Plummer | |
| 2009/0088897 | A1* | 4/2009 | Zhao | A61B 34/37 700/250 |
| 2013/0211590 | A1 | 8/2013 | Diolaiti et al. | |
| 2013/0245375 | A1* | 9/2013 | DiMaio | A61B 34/30 600/166 |
| 2014/0055489 | A1 | 2/2014 | Itkowitz et al. | |
| 2014/0135792 | A1 | 5/2014 | Larkin et al. | |
| 2014/0249520 | A1 | 9/2014 | Ghaffari et al. | |
| 2014/0282194 | A1* | 9/2014 | Nikou | G06F 3/04842 715/771 |
| 2014/0309659 | A1 | 10/2014 | Roh et al. | |
| 2014/0316433 | A1 | 10/2014 | Navve et al. | |
| 2015/0012010 | A1 | 1/2015 | Adler et al. | |
| 2015/0053749 | A1* | 2/2015 | Shelton, IV | A61B 90/96 227/181.1 |
| 2015/0161802 | A1 | 6/2015 | Christiansen | |
| 2015/0351864 | A1 | 12/2015 | Kamon et al. | |
| 2016/0314717 | A1 | 10/2016 | Grubbs | |
| 2017/0172674 | A1 | 6/2017 | Hanuschik et al. | |
| 2017/0231701 | A1 | 8/2017 | Cohen et al. | |
| 2018/0064499 | A1 | 3/2018 | Itkowitz et al. | |
| 2018/0085926 | A1 | 3/2018 | Kogan | |
| 2021/0093402 | A1 | 4/2021 | Mustufa et al. | |

FOREIGN PATENT DOCUMENTS

| JP | 2001104333 A | 4/2001 |
| WO | WO-0030548 A1 | 6/2000 |
| WO | WO-2008002830 A2 | 1/2008 |
| WO | WO-2010117685 A2 | 10/2010 |
| WO | WO-2011060139 A2 | 5/2011 |
| WO | WO-2014104088 A1 | 7/2014 |
| WO | WO-2014160086 A2 | 10/2014 |
| WO | WO-2015023665 A1 | 2/2015 |
| WO | WO-2016023123 A1 | 2/2016 |
| WO | WO-2017160086 A1 | 9/2017 |
| WO | WO-2018013197 A1 | 1/2018 |

OTHER PUBLICATIONS

International Preliminary Report on Patentability for Application No. PCT/US2017/029380, dated Jan. 24, 2019, 6 pages (ISRG08340/PCT).

International Search Report and Written Opinion for Application No. PCT/US2017/029380, dated Aug. 8, 2017, 13 pages (ISRG08340/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR ONSCREEN MENUS IN A TELEOPERATIONAL MEDICAL SYSTEM

CROSS REFERENCE TO RELATED APPLICATIONS

This patent application is a continuation of U.S. application Ser. No. 17/061,785 (filed Oct. 2, 2020), which is a divisional of U.S. application Ser. No. 16/316,981 (filed Jan. 10, 2019), which is the U.S. national phase of International Application No. PCT/US2017/029380, filed Apr. 25, 2017, which designated the U.S. and claims priority to and the benefit of the filing date of U.S. Provisional Application No. 62/362,376 entitled "SYSTEMS AND METHODS FOR ONSCREEN MENUS IN A TELEOPERATIONAL MEDICAL SYSTEM," filed Jul. 14, 2016, all of which are incorporated herein by reference in their entirety.

FIELD

The present disclosure is directed to systems and methods for performing a teleoperational medical procedure and more particularly to systems and methods for displaying function menus for teleoperational instruments used in a surgical environment.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. As teleoperational medical systems become more complex, with additional features and interaction modalities, adding additional physical control devices to the operator control station becomes less feasible. To extend the capability of a teleoperational system, graphical menus visible to and accessible by the operator are needed.

SUMMARY

The embodiments of the invention are summarized by the claims that follow below.

In one embodiment, a system comprises a teleoperational assembly including an operator control system and a first teleoperational manipulator configured for operation by an operator control device of the operator control system. The first teleoperational manipulator is configured to control the operation of a first medical instrument in a surgical environment. The system also comprises a processing unit including one or more processors. The processing unit is configured to display an image of a field of view of the surgical environment and display a menu proximate to an image of the first medical instrument in the image of the field of view. The menu includes at least one icon representing a function for the first medical instrument.

In another embodiment, a method comprises displaying an image of a field of view of a surgical environment. A first medical instrument in the field of view is coupled to a first manipulator in a teleoperational assembly. The method further comprises displaying a menu proximate to an image of the first medical instrument in the image of the field of view. The menu includes a plurality of icons wherein each icon is associated with a function for the first medical instrument. The method further includes identifying a selected icon from the plurality of icons based upon a movement of an operator control device of a teleoperational operator control system.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
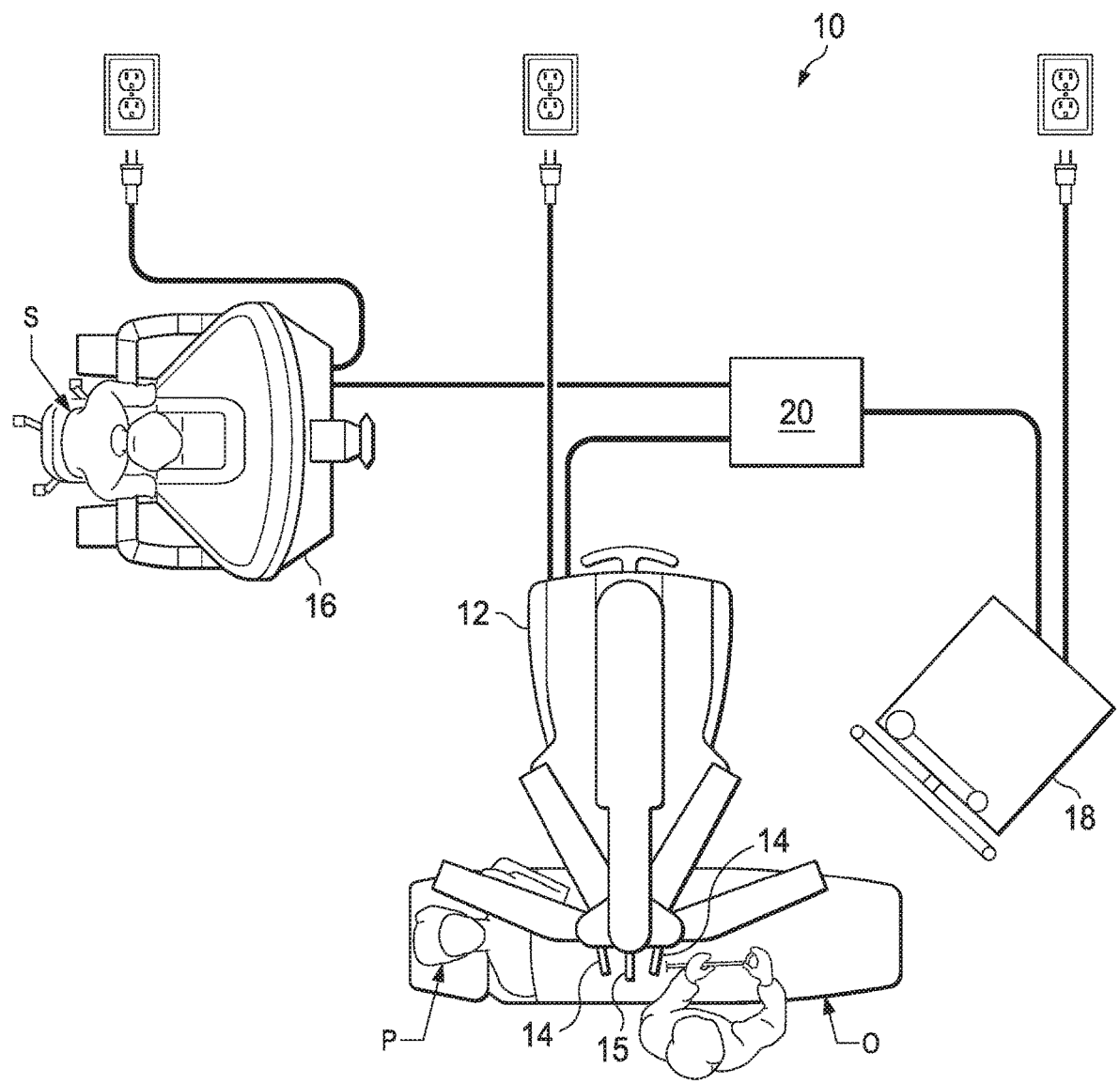
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart. A medical instrument system 14 (also called "medical instrument 14") and an endoscopic imaging system 15 (also called "endoscope 15") are operably coupled to the teleoperational assembly 12. An operator input system 16 allows a surgeon or other type of clinician S to view images of or representing the surgical site and to control the operation of the medical instrument system 14 and/or the endoscopic imaging system 15.

The operator input system 16 may be located at a surgeon's console or other control console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the operator input system 16. An image of the surgical site can be obtained by the endoscopic imaging system 15, such as a stereoscopic endoscope, which can be manipulated by the teleoperational assembly 12 to orient the endoscopic imaging system 15. An electronics system 18 (also called an "electronics cart 18" when configured as a cart or configured to be usable as part of a cart) can be used to process the images of the surgical site for subsequent display to the surgeon S through the surgeon's console comprising the operator input system 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The teleoperational medical system 10 also includes a control system 20. The control system 20 includes at least one memory and at least one processor (not shown), and typically a plurality of processors, for effecting control between the medical instrument system 14, the operator input system 16, and an electronics system 18. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The electronics system 18 can be coupled with the endoscopic imaging system 15 and can include a processor to process captured images for subsequent display, such as to a surgeon on the surgeon's console, or on another suitable display located locally and/or remotely. For example, where a stereoscopic endoscope is used, the electronics system 18 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. The electronics system 18 may also include a display monitor and components of the control system 20.

The teleoperational medical system 10 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
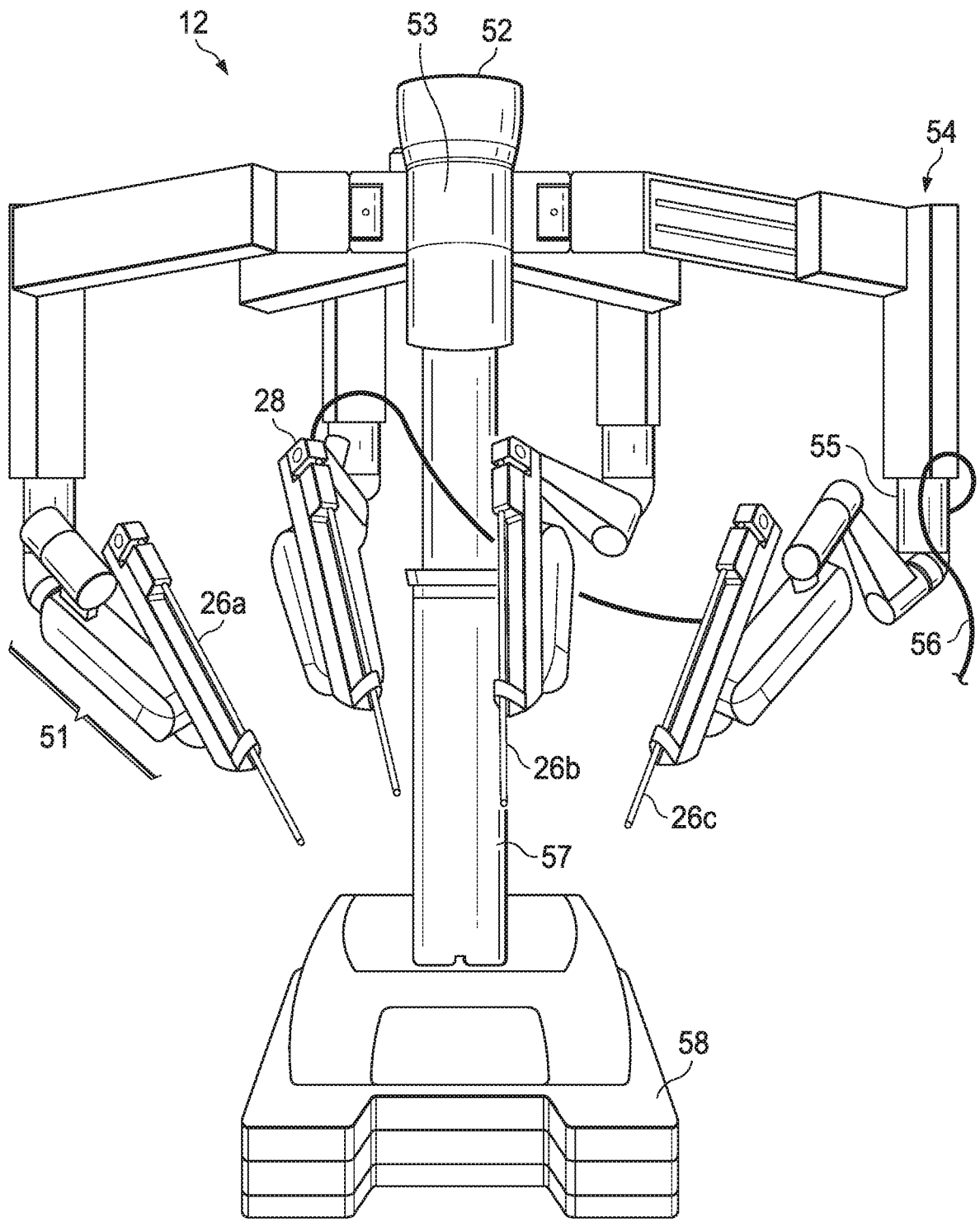
FIG. 1B is a perspective view of a patient side cart, according to one example of principles described herein.

FIG. 1B is a perspective view of one embodiment of a teleoperational assembly 12 which may be referred to as a patient side cart 12 when designed to be placed near the patient during a medical operation. The teleoperational assembly 12 shown provides for the manipulation of three surgical instruments 26a, 26b, 26c (e.g., instrument systems 14) and an imaging instrument 28 (e.g., endoscopic imaging system 15), such as a stereoscopic endoscope used for the capture of images of the site of the procedure. The imaging device 28 may also be called "imaging device 28," and may transmit signals over a cable 56 to the control system 20. Manipulation is provided by teleoperative mechanisms having a number of joints. The imaging device 28 and the surgical instruments 26a-c can be positioned and manipulated through incisions in the patient so that a kinematic remote center is maintained at the incision to minimize the size of the incision. Images of the surgical site can include images of the distal ends of the surgical tools 26a-c when they are positioned within the field-of-view of the imaging device 28.

The patient side cart 22 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The patient side cart 22 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument 26. The manipulator arms 51 may be teleoperatable. In some examples, the arms 54 connecting to the orienting platform are not teleoperatable. Rather, such arms 54 are positioned as desired before the surgeon S begins operation with the teleoperative components.

Endoscopic imaging systems (e.g., systems comprising imaging device 15 or 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
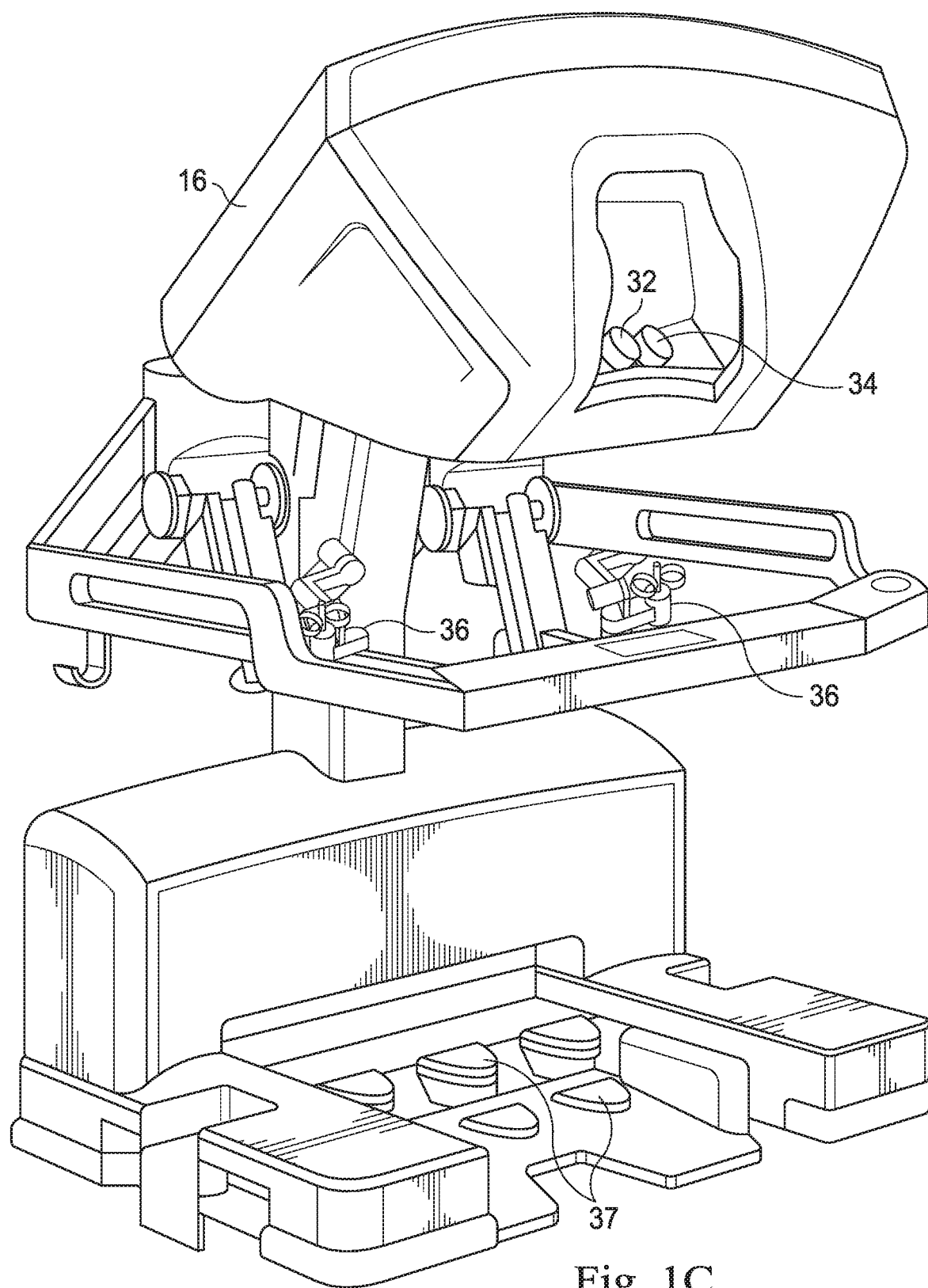
FIG. 1C is a perspective view of a surgeon's control console for a teleoperational medical system, in accordance with many embodiments.

FIG. 1C is a perspective view of a surgeon's console comprising the operator input system 16. The surgeon's console comprising the operator input system 16 includes a left eye display 32 and a right eye display 34 for presenting the surgeon S with a coordinated stereo view of the surgical environment that enables depth perception. The console comprising the operator input system 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot.

Figure 2:
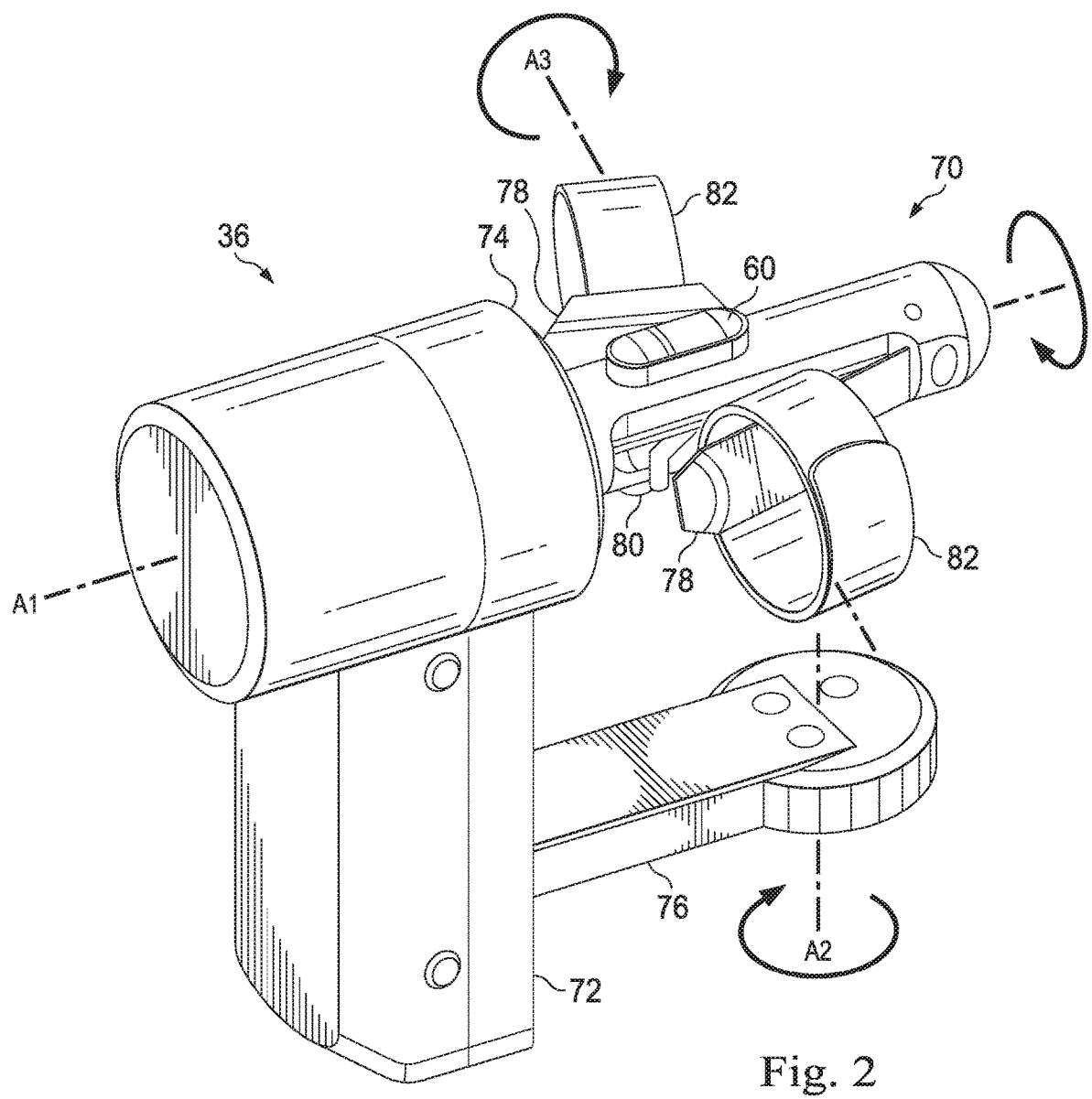
FIG. 2 illustrates an input control device of the surgeon's control console.

With reference to FIG. 2, each control device 36 includes a four degree of freedom gimbal or wrist that allows rotation of an actuatable handle 70 about three axes-axis A1, axis A2, and axis A3. The handle 70 is coupled to a first elbow-shaped link 72 by a first rotatable joint 74 that permits continuous rotation of the handle. The first link 72 is coupled to a platform 76. Each control device 36 will generally allow movement of the handle 70 within the workspace control workspace with a plurality of degrees of freedom, typically with six degrees of freedom, three rotational degrees of freedom and three translational degrees of freedom. This allows the actuatable handle 70 to be moved to any position and any orientation within its range of motion. The actuatable handle 70 includes grip actuators 78 and/or switches 80 to allow the operator to actuate the instrument 26 or 28 being positioned by the motion of the handle. Finger loops 82 are attached to the handle 70 to prevent the operator's fingers from slipping on the handle.

The surgeon's console comprising the operator input system 16 provides a "head-in" graphical user interface which allows the surgeon to perform a variety of functions with the medical instruments while his or her head remains in the console comprising the operator input system 16 with eyes viewing the displays 32, 34 and with hands remain engaged with the control devices 36. As will be described below, an example of a procedure that may be performed while the user's head remains in the console comprising the operator input system 16 is an instrument exchange procedure. As features and interaction modalities of the teleoperational system and medical instruments increase, it becomes impracticable to continue to add additional physical input control devices (e.g., foot pedals, switches, buttons) for each additional feature. Including graphical menus in the user interface provide a rich, extensible platform to access instrument and system capabilities without adding additional physical user inputs.

Figure 3:
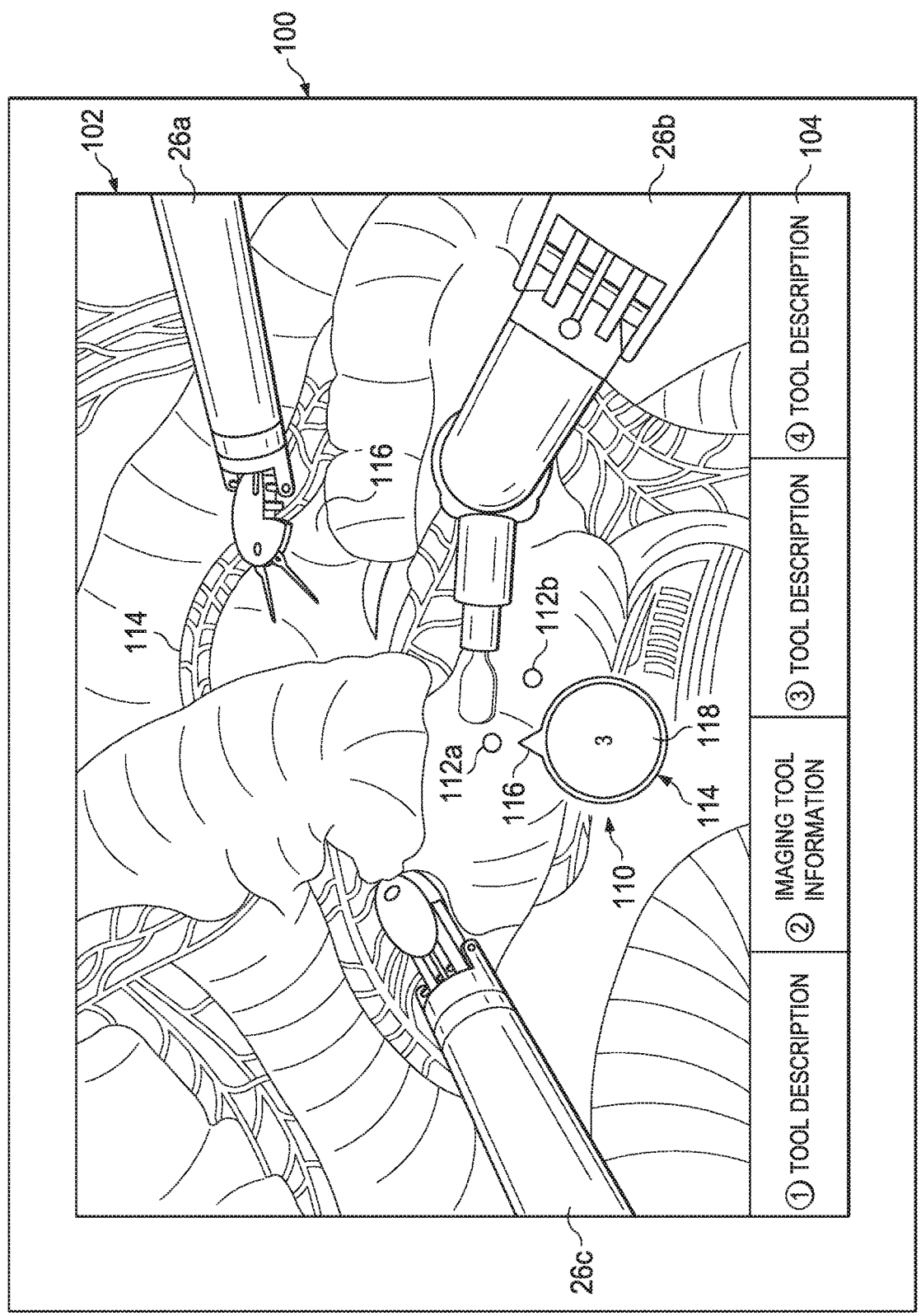
FIG. 3 illustrates a field of view of a surgical environment with a graphical menu proximate to a medical instrument in the field of view.

FIG. 3 illustrates a surgical environment 100 within the patient P. An imaging instrument (e.g., imaging instrument 28) is used to display an image 102 of the imaging instrument's field of view within the surgical environment 100. The image 102 may be a three dimensional image obtained by a stereoscopic endoscope and generated as a composite image of the images visible to a user through right and left eye displays. The field of view includes an image of a distal end portion of instrument 26a, a distal end portion of instrument 26b, and a distal end portion of instrument 26c. The image 102 also includes information fields 104 located at the periphery of the image which may include instructions to the clinician, warnings, instrument identification information, status information, or other information relevant to the surgical procedure.

In one embodiment, as shown in FIG. 3, accessing features and capabilities for the instrument 26b in the field of view is enabled by a graphical menu 110 superimposed on the image 102. The graphical menu 110 is displayed proximate to image of the distal end of the medical instrument 26b so that the surgeon can easily tell that the co-located graphical menu 110 pertains to the medical instrument 26b. In this embodiment, a graphical menu 110 contains association information related to the medical instrument 26b, such as a numerical identifier of the teleoperational arm (e.g. Arm "3") to which the instrument is coupled. "Systems and Methods for Onscreen Identification of Instruments in a Teleoperational Medical System" are provided in U.S. Provisional App. No. 62/134,297, filed Mar. 17, 2015, which is incorporated by reference herein in its entirety.

In some embodiments, a default location for placement of the graphical menu 110 is superimposed over a portion of the distal end of instrument 26b. In other embodiments, the graphical menu 110 is displayed adjacent to the distal end portion. The default location for the menu may depend upon the size of the distal end portion of the medical instrument 26b in the field of view. For example, if the image is closely zoomed in and the end effector occupies a large portion of the image, the menu may be located on a proximal portion of one of the end effector jaws without obstructing the view at the distal end of the jaws. If, however, the image is zoomed out and the end effector jaws are relatively small in the image, the menu may be located on the joint region or the shaft to avoid obscuring the jaws. The placement of the menu 110 allows the clinician to access features of the instrument while remaining focused on the surgical environment.

The graphical menu 110 has a minimized configuration in which functions associated with instrument 26b are presented as small, minimized function icons 112a, 112b radially arranged about the periphery of a selector icon 114. The selector icon 114 includes a pointer 116 and a body 118. In this embodiment, the numerical identifier for the teleoperational arm is located in a central region of the body 118. Responsive to movement of the control device 36 associated with the instrument 26b, the selector icon 114 is animated to pivot about the center of the body 118 to move the pointer 116 in a dial-like fashion.

Figure 4:
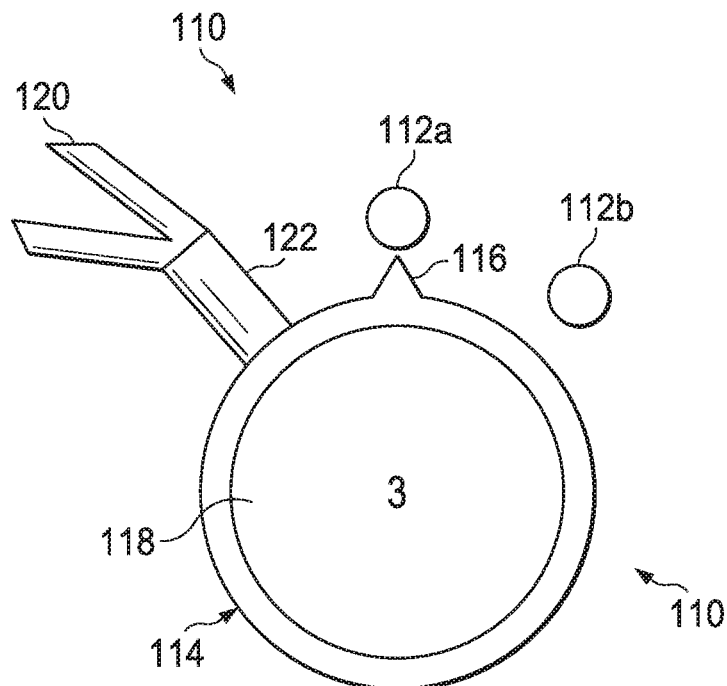
FIG. 4 illustrates a minimized graphical menu.
Figure 8A:
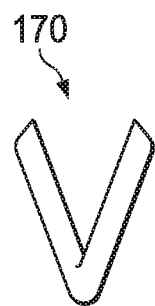
FIGS. 8A-8C illustrate grip icons according to embodiments of this disclosure.
Figure 8B:
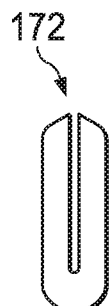
Figure 8C:
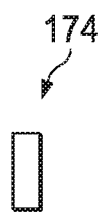

As shown in FIG. 4, the graphical menu 110 may, optionally, include a grip indicator 120 that indicates the state of the end effector of the instrument 26b and a shaft indicator 122 that indicates the direction of the shaft of the instrument 26b. If the instrument 26b has a two-grip end effector, the grips may be shown as an open grip indicator 170 (FIG. 8A) or a closed grip indicator 172 (FIG. 8B). If the instrument 26b has a single blade end effector, the blade may be shown as a single finger 174 (FIG. 8C). The indicators 120, 122 assist the viewing surgeon by helping to understand which instrument the graphical menu is associated with. For example, where there is ambiguity about the association between menu and instrument, the surgeon may view the indicators 120, 122 and observe the configuration of the nearby instrument distal ends. The surgeon can then associate the nearby instrument with the end effector and shaft configurations that match the indicators 120, 122.

Figure 5:
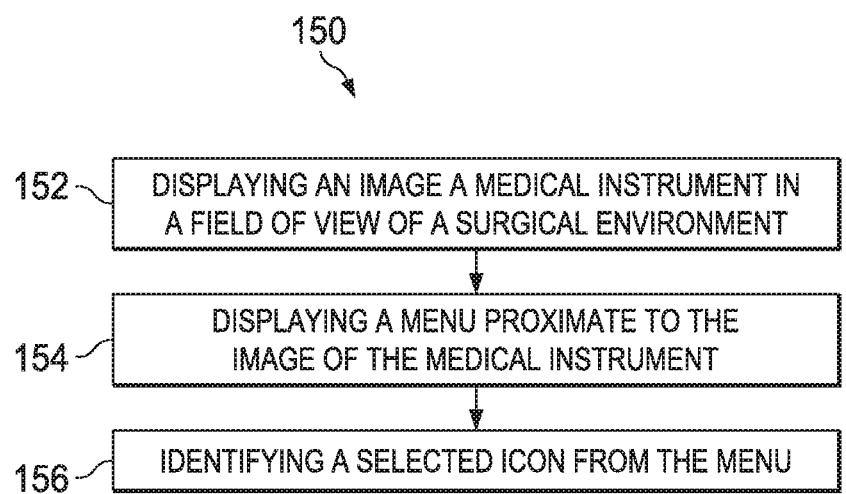
FIG. 5 illustrates a method for accessing features for a medical instrument.

FIG. 5 illustrates a method 150 for accessing features for the medical instrument 26b or the coupled teleoperational arm 3 via the graphical menu 110. At a process 152, the field of view image 102 is displayed while the teleoperational system is in a surgical instrument control or "following" operational mode in which the movement of the instruments, including instrument 26b follows the movements of the user's hand in the associated control device 36. At a process 154, the surgeon causes the teleoperational system to enter into a menu mode in which movement of the user's hand in the associated control device 36 is decoupled from movement of the instrument 26b and arm 3. In one embodiment, the menu mode may be entered when the surgeon steps on a clutch pedal (e.g., pedal comprising the input control device 37) of the console comprising the operator input system 16. After depressing the clutch pedal, control of the medical instrument 26b by the control device 36 is suspended. The control device 36 may move freely without corresponding movement of the medical instrument 26b. In the menu mode, movement of the grip actuators 78 of the control device 36 is decoupled from the movement of the instrument 26b end effector. The minimized graphical menu 110 appears upon entry into the menu mode.

Figure 6:
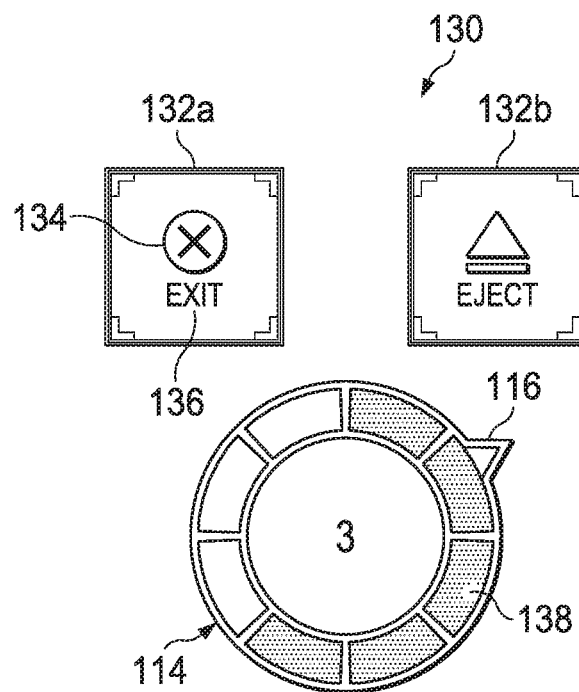
FIG. 6 illustrates an opened graphical menu.

To provide greater information about each of the functions associated with indicators 120, 122, an expanded graphical menu 130 may be displayed, as shown in FIG. 6. Graphical menu 130 includes the selector icon 114 and replaces the minimized function icons 112a, 112b with expanded function icons 132a, 132b. In this embodiment, each of the expanded function icons includes a pictogram 134 and a function label 136 that describe the function associated with the function icon. For example, icon 132a is associated with an "EXIT" function that returns the expanded menu 130 to the format of the minimized graphical menu 110. Icon 132b is associated with an "EJECT" function which initiates an instrument ejection sequence for the medical instrument 26b. The expanded graphical menu 130 is displayed when the handle 70 of the control device 36 is rotated about axis A1. Optionally, when the handle 70 is rotated, a haptic force providing a "click" sensation, will be provided to the surgeon through the control device 36 to provide confirmation of the launch of the graphical menu 130.

The rotational movement of the handle 70 (about axis A1) used to open the expanded graphical menu 130 or to move the selector icon 114 is movement in a degree of freedom (i.e. the roll degree of freedom) that is not used to operate the instruments when the system is in other modes of operation such as the surgical instrument control mode. Thus, the surgeon may recognize that the roll degree of freedom about the axis of the control device is decoupled and used for menu selection, not instrument operation. The orientation of the roll axis does not change in the menu mode (or generally when the clutch pedal is engaged) and is maintained in alignment with the last orientation of the instrument end effector. In other embodiments, the same degrees of freedom used to control the selector icon may be used to control tool movement in the surgical instrument control mode.

Returning to FIG. 5, at a process 156, one of the function icons 132a, 132b may be identified from the menu 130. More specifically when the expanded graphical menu 130 is first opened, the pointer 116 is positioned in a neutral position such as upward, toward the icon 132a. This neutral position of the pointer corresponds to a neutral position of the control device. The neutral position of the control device may be the most recent position of the control device in the instrument control mode. In other embodiments, the pointer is directed in other radial directions in the neutral position. In the embodiment of FIG. 6, when the handle 70 is rotated clockwise about axis A1, the pointer 116 rotates clockwise from the neutral position toward the next function icon 132b.

The handle 70 may be rotated, for example, less than 180° or even less than 90° to cause the pointer 116 to move to next function icon. In this example, the handle 70 is rotated approximately 40°. A haptic force, e.g., a "click" sensation, may be provided to the surgeon through the control device 36 to provide confirmation that the pointer 116 is pointed at the next function icon 132b in the radial sequence of icons.

After the clockwise turn of the handle 70 and the application of the corresponding haptic force, the handle returns or "snaps back" to the neutral position, but the pointer 116 remains pointed at the function icon 132b. The return to neutral position allows minimal deviation of the pose of the surgeon's hand to provide for better ergonomics (e.g., the surgeon's wrist is not required to turn excessively). This recentering of the handle 70 also allows reentry into the instrument control mode to proceed more quickly. Although only two function icons are shown, in other embodiments, function icons may be arranged around the full circle of the selector icon. After each rotation of the handle 70, the pointer advances to the next icon in the radial series, but the control device 36 may return to the neutral position. The handle 70 may also be moved counter-clockwise about the axis A1 to cause the pointer 116 to move counterclockwise.

Figure 9A:
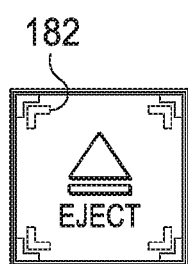
FIG. 9A illustrates an icon associated with an active state of a function.
Figure 9B:
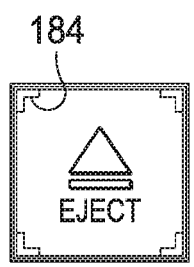
FIG. 9B illustrates an icon associated with a selected state of a function.
Figure 9C:
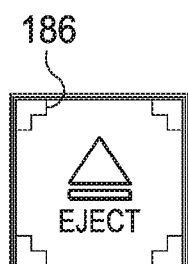
FIG. 9C illustrates an icon associated with an enabled state of a function.
Figure 9D:
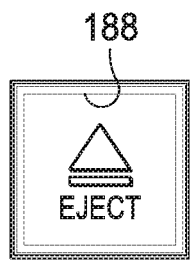
FIG. 9D illustrates an icon associated with an unavailable function.

The functions that are available for selection may be identified by a graphic characteristic of the icon. For example, disabled functions may be indicated by color (e.g., a white pictogram and text), by a graphic feature such as a box 188 (FIG. 9D), or by an "X" placed over the pictogram and/or text. Enabled functions may be indicated by color and/or by corner brackets 186 of a predetermined size. (FIG. 9C)

When the pointer 116 is directed at the function icon 132b, that function icon is considered "selected." The selected function may be indicated by a change in the appearance of the function icon 132b. For example, the corner brackets 184 may have a narrower width as compared to the corner brackets 186 in the enabled state. (FIG. 9B)

To activate the function associated with the icon 132b, the surgeon depresses the grip actuators 78 or other buttons or switches at the control console comprising the operator input system 16. In this embodiment, the icon 132b is associated with an EJECT function, and depressing the grip actuators initiates the instrument ejection sequence. When the selected function has been activated, the appearance of the function icon 132 may change to indicate that the function is selected. For example, double corner brackets 182 may appear to indicate to the viewer that the EJECT function has been activated. (FIG. 9A)

The instrument ejection sequence may begin with a brief hold-off period. This period may be marked by a change in the graphical menu such as a progressive change in color of the selector icon or the incremental growth of a ring around the edge of the selector icon. Next, if the instrument has a two-finger grip end effector, the grips open to release any tissue and the wrist of the instrument straightens into alignment with the instrument shaft. The shaft may retract slightly. During these stages of the EJECT function, a progress indicator 138 on the selector icon 114 indicates the current stage of the EJECT function. For example, the progress indicator 138 may be a graphic ring that incrementally changes color, proceeding in a clockwise direction. Before the graphic ring creates a full circle, the EJECT function may be cancelled by, for example, opening the grips of the control device or releasing the clutch pedal. After the progress indicator 138 indicates that the instrument is straightened, the instrument may be retracted in to the access cannula along the insertion axis of the cannula. During the retraction process that brings the end effector into the cannula, the EJECT function may not be interrupted.

The menu of FIG. 6 may be controlled by the surgeon's right hand in the corresponding control device. For left hand controlled instruments, the icons may be arranged with an opposite configuration (i.e., the EJECT icon to the left of the END icon). In various embodiments, movement of the selector icon 114 may be coupled to the right or, alternatively, the left hand control device. Different graphical user interface menus maybe associated with each hand so that the right hand selects from a first menu and the left hand selects from a second menu. The menu may, alternatively, be configured so that the menu items are selected by counter-clockwise rotation. In other embodiments, the control device may move in both clockwise and counterclockwise directions to select menu items. In various alternative embodiments, more than one graphical menu may be co-located with the tips of the instrument in the image of the field of view.

Figure 7:
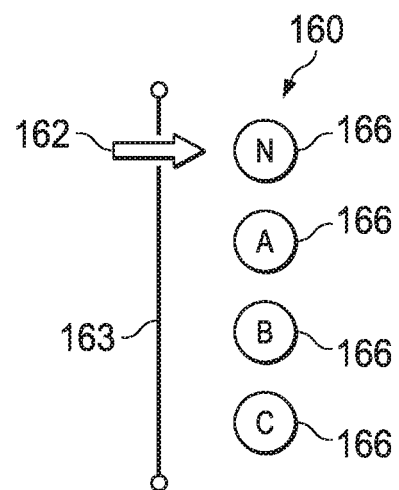
FIG. 7 illustrates another graphical menu.

FIG. 7 illustrates a graphical menu 160 according to an alternative embodiment. In this embodiment a selector icon 162 moves downward along a linear path 163 in response to clockwise rotation of the control device handle 70 and upward in response to counterclockwise rotation of the control device handle. The function icons 164 are linearly aligned along the linear path 163. The selection and activation processes for this embodiment in which the icons are linearly aligned are generally the same as described above when the icons are radially arranged.

Figure 10:
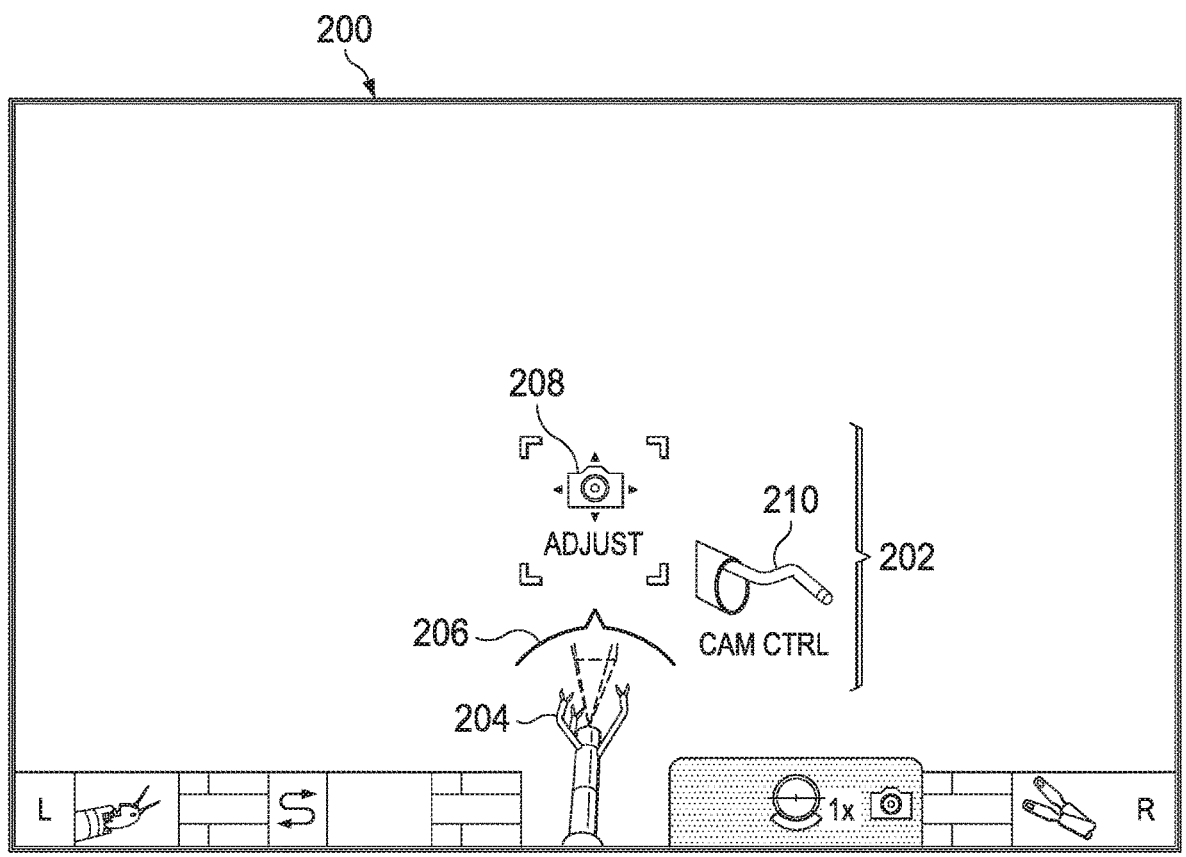
FIG. 10 illustrates a graphical user interface according to another embodiment of this disclosure.
Figure 11:
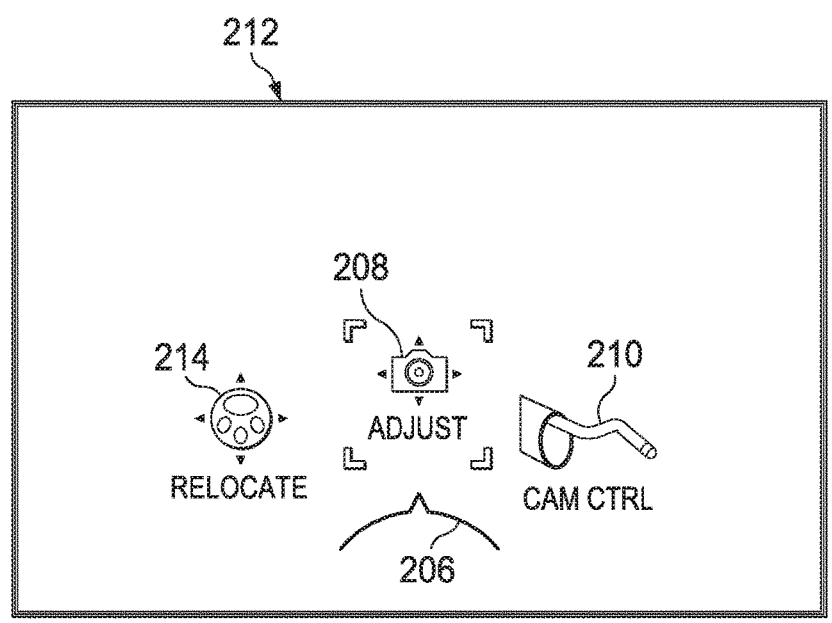
FIG. 11 illustrates a graphical menu according to another embodiment of this disclosure.

FIG. 10 illustrates a graphical user interface 200 according to another embodiment of this disclosure. In this embodiment, a graphical menu 202 may be associated with a global control mode selection rather than with a particular instrument or instrument drive. In this embodiment, the menu 202 is in a fixed location in the surgical view, centered over a graphical image 204 of an instrument navigator representing a component of the teleoperational system. For example, the instrument navigator may represent the configuration of the end effectors of the system. The menu 202 appears when the surgeon enters an ADJUST-CONTROL mode by manipulating a control device (e.g., a clutch foot pedal) on the control console. The menu includes a selector icon 206, which in this embodiment includes a partial circular shape with a pointer, and radially arranged function icons 208, 210. In an initial position, the selector icon may be pointed upright to indicate the current active control mode. The selector icon 206 may be pivoted, as described, above by turning the control handle 70 about the roll axis A1. When the handle is turned approximately 40° clockwise, the pointer of the selector icon 206 is directed toward the function icon 208 to select a camera-control function. As previously described, a haptic force may be provided to give the surgeon a "click" sensation when the selector icon reaches the icon 208. The function may be selected by squeezing the grip actuators 78. Once in camera-control mode, the selector icon 206 may disappear. The camera-control mode may be exited when the surgeon releases the foot pedal. As previously described, the handle 70 of the control device may return to a neutral position after each click of the selector icon 206. FIG. 11 illustrates a modified graphical menu 212 that further includes an icon 214 for the function of relocate control. In this embodiment, the icon 214 is to the left of the icon 208 so the surgeon may rotate the selector icon 206 counter-clockwise.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A teleoperational medical system comprising:
   a teleoperational assembly including:
      an operator control system;
      a first teleoperational manipulator configured for operation by an operator control device of the operator control system;
      a first medical instrument, wherein the first teleoperational manipulator is configured to control operation of the first medical instrument in a surgical environment; and
      a processing unit including one or more processors, wherein the processing unit is configured to:
         display an image of a field of view of the surgical environment, and
         display a menu proximate to an image of the first medical instrument in the image of the field of view, wherein the menu includes at least one state indicator representing a state of a component of the first medical instrument.

2. The teleoperational medical system of claim 1, wherein the first medical instrument comprises a shaft and the at least one state indicator comprises a shaft indicator that represents a state of the shaft.

3. The teleoperational medical system of claim 2, wherein the state of the shaft is a direction of the shaft.

4. The teleoperational medical system of claim 1, wherein the first medical instrument comprises an end effector and the at least one state indicator comprises an end effector indicator that represents a state of the end effector.

5. The teleoperational medical system of claim 4, wherein the end effector comprises a grip and the end effector indicator represents an open state or a closed state of the grip.

6. The teleoperational medical system of claim 4, wherein the end effector comprises a blade and the end effector indicator represents a state of the blade.

7. The teleoperational medical system of claim 1, further comprising a second medical instrument, wherein the at least one state indicator is configured to assist a user in determining the menu is associated with the first medical instrument.

8. The teleoperational medical system of claim 1, wherein the processing unit is configured to display the menu after disabling the operator control device from controlling operation of the first medical instrument.

9. The teleoperational medical system of claim 8, wherein the processing unit is configured to disable the operator control device in response to activation of a clutch mechanism of the operator control system.

10. The teleoperational medical system of claim 1, wherein the teleoperational assembly further includes:
   a second teleoperational manipulator configured for operation by the operator control device, wherein the menu further includes an identifier indicating the first medical instrument is coupled to the first teleoperational manipulator.

11. A method for displaying menus in a teleoperational medical system comprising:
   displaying an image of a field of view of a surgical environment, wherein a first medical instrument in the field of view is coupled to a first manipulator in a teleoperational assembly; and
   displaying a menu proximate to an image of the first medical instrument in the image of the field of view, the menu including at least one state indicator representing a state of a component of the first medical instrument.

12. The method of claim 11, wherein the at least one state indicator comprises a shaft indicator that represents a state of a shaft of the first medical instrument.

13. The method of claim 12, wherein the state of the shaft is a direction of the shaft.

14. The method of claim 11, wherein the at least one state indicator comprises an end effector indicator that represents a state of an end effector of the first medical instrument.

15. The method of claim 14, wherein the end effector comprises a grip and the end effector indicator represents an open state or a closed state of the grip.

16. The method of claim 14, wherein the end effector indicator represents a state of a blade of the end effector.

17. The method of claim 11, wherein the at least one state indicator is configured to assist a user in determining the menu is associated with the first medical instrument.

18. The method of claim 11, further comprising:
   receiving a command to disable an operator control device from controlling operation of the first medical instrument before displaying the menu.

19. The method of claim 18, wherein receiving the command to disable the operator control device is caused by activation of a clutch mechanism of an operator control system.

20. The method of claim 11, further comprising:
   displaying an identifier in the menu indicating the first medical instrument is coupled to the first teleoperational manipulator.

21. A teleoperational medical system comprising:
   a first teleoperational manipulator for manipulating a medical instrument;
   an operator control system movable in a plurality of degrees of freedom for controlling the first teleoperational manipulator; and
   a processing unit including one or more processors to display a menu for adjusting functions of the teleoperational medical system and allow navigation of the menu using two or more degrees of freedom of the operator control system.

22. The teleoperational medical system of claim 21, wherein the two or more degrees of freedom include a roll degree of freedom of the operator control system.

* * * * *